United States Patent [19]

Jørgensen et al.

[11] Patent Number: 5,750,518
[45] Date of Patent: May 12, 1998

[54] HETEROCYCLIC COMPOUNDS

[75] Inventors: Tine Krogh Jørgensen, Herlev; Knud Erik Andersen, Smørum; Henrik Sune Andersen, København; Rolf Hohlweg, Kvistgaard; Peter Madsen, Bagsværd; Uffe Bang Olsen, Vallensbæk, all of Denmark

[73] Assignee: Novo Nordisk A/S, Bagsværd, Denmark

[21] Appl. No.: 863,751

[22] Filed: May 27, 1997

Related U.S. Application Data

[62] Division of Ser. No. 623,807, Mar. 29, 1996.

[30] Foreign Application Priority Data

| Apr. 7, 1995 | [DK] | Denmark | 0403/95 |
| Sep. 11, 1995 | [DK] | Denmark | 1006/95 |

[51] Int. Cl.$^6$ .......... A61K 31/40; A61K 31/445; C07D 207/12; C07D 211/60
[52] U.S. Cl. .......... 514/183; 540/451; 540/460; 540/471; 540/479
[58] Field of Search .......... 514/183, 540/451, 540/460, 471, 479

[56] References Cited

U.S. PATENT DOCUMENTS

| 3,336,293 | 8/1967 | Cusic et al. | 260/239 |
| 3,514,443 | 5/1970 | Yale et al. | 260/239 |
| 3,803,143 | 4/1974 | Tanaka et al. | 260/247.1 |
| 4,904,688 | 2/1990 | Rae et al. | 514/450 |
| 5,354,747 | 10/1994 | Hansen, Jr. et al. | 514/211 |

FOREIGN PATENT DOCUMENTS

| 1084267 | 6/1960 | Germany . |
| 1109847 | 4/1968 | United Kingdom . |
| WO 92/202658 | 11/1992 | WIPO . |

Primary Examiner—Mukund J. Shah
Assistant Examiner—Deepak R. Rao
Attorney, Agent, or Firm—Steve T. Zelson; Elias J. Lambiris

[57] ABSTRACT

The present invention relates to novel N-substituted azaheterocyclic carboxylic acids and esters thereof in which a substituted alkyl chain forms part of the N-substituent or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation.

25 Claims, No Drawings

HETEROCYCLIC COMPOUNDS

CROSS-REFERENCE TO RELATED APPLICATIONS

This application is a divisional application of Ser. No. 08/623,807 filed Mar. 29, 1996 and claims priority under 35 U.S.C. 119 of Danish application 0403/95 and 1006/95 filed Apr. 7, 1995 and Sep. 11, 1995, respectively, the contents of which are fully incorporated herein by reference.

FIELD OF THE INVENTION

The present invention relates to novel N-substituted azaheterocyclic carboxylic acids and esters thereof in which a substituted alkyl chain forms part of the N-substituent or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation. The invention also relates to the use of the present compounds for the treatment of insulin resistance in non-insulin-dependent diabetes mellitus (NIDDM) or aging, the present compounds knowing to interfere with neuropeptide containing C-fibres and hence inhibit the secretion and circulation of insulin antagonizing peptides like CGRP or amylin.

BACKGROUND OF THE INVENTION

The nervous system exerts a profound effect on the inflammatory response. Antidromic stimulation of sensory nerves results in localized vasodilation and increased vascular permeability (Janecso et al. Br. J. Pharmacol. 1967, 31, 138–151) and a similar response is observed following injection of peptides known to be present in sensory nerves. From this and other data it is postulated that peptides released from sensory nerve endings mediate many inflammatory responses in tissues like skin, joint, urinary tract, eye, meninges, gastro-intestinal and respiratory tracts. Hence inhibition of sensory nerve peptide release and/or activity, may be useful in treatment of, for example arthritis, dermatitis, rhinitis, asthma, cystitis, gingivitis, thrombophlebitis, glaucoma, gastro-intestinal diseases or migraine.

Further, the potent effects of CGRP on skeletal muscle glycogen synthase activity and muscle glucose metabolism, together with the notion that this peptide is released from the neuromuscular junction by nerve excitation, suggest that CGRP may play a physiological role in skeletal muscle glucose metabolism by directing the phosphorylated glucose away from glycogen storage and into the glycolytic and oxidative pathways (Rossetti et al. Am. J. Physiol. 264, E1–E10, 1993). This peptide may represent an important physiological modulator of intracellular glucose trafficking in physiological conditions, such as exercise, and may also contribute to the decreased insulin action and skeletal muscle glycogen synthase in pathophysiological conditions like NIDDM or aging-associated obesity (Melnyk et al. Obesity Res. 3, 337–344, 1995) where circulating plasma levels of CGRP are markedly increased. Hence inhibition of release and/or activity of the neuropeptide CGRP may be useful in the treatment of insulin resistance related to type 2 diabetes or aging.

In U.S. Pat. Nos. 4,383,999 and 4,514,414 and in EP 236342 as well as in EP 231996 some derivatives of N-(4,4-disubstituted-3-butenyl)azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as GABA uptake inhibitors. EP 221572 claims that 1-aryloxyalkylpyridine-3-carboxylic acids are inhibitors of GABA uptake.

DESCRIPTION OF THE INVENTION

The present invention relates to novel N-substituted azaheterocyclic carboxylic acids and esters thereof of formula I

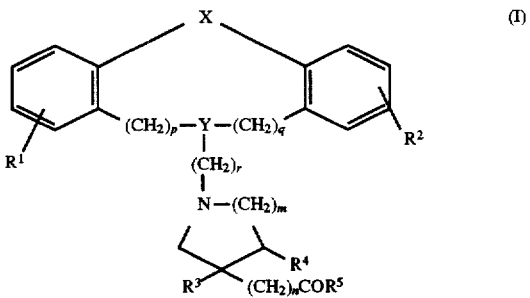

wherein $R^1$ and $R^2$ independently are hydrogen, halogen, trifluoromethyl, hydroxy, $C_{1-6}$alkyl or $C_{1-6}$-alkoxy; and Y is —CH$_2$—N—CH$_2$—, —CH$_2$—N—CH$_2$—, —(C=O)—N—CH$_2$—, —CH$_2$—N—(C=O)—, —CH$_2$—C=CH—, —CH=C—CH$_2$—, —CH$_2$—CH—CH$_2$—, —CH$_2$—CH—CH$_2$—, —CH$_2$—C=CH—, —CH=C—CH$_2$—, —O—CH—CH$_2$—, —CH$_2$—CH—O—, —S—CH—CH$_2$— or —CH$_2$—CH—S— wherein only the underscored atoms participate in the ring system; and X is —O—, —S—, —C($R^6R^7$)—, —CH$_2$CH$_2$—, —CH=CH—CH$_2$—, —CH$_2$—CH=CH—, —CH$_2$—(C=O)—, —(C=O)—CH$_2$—, —CH$_2$CH$_2$CH$_2$—, —CH=CH—, —N($R^8$)—(C=O)—, —(C=O)—N($R^8$)—, —O—CH$_2$—, —CH$_2$—O—, —S—CH$_2$—, —CH$_2$—S—, —(C=O)—, —N($R^9$)— or —(S=O)— wherein $R^6$, $R^7$, $R^8$ and $R^9$ independently are hydrogen or $C_{1-6}$-alkyl; and q is 0 or 1; and p is 0 or 1; and r is 1, 2 or 3; and m is 1 or 2; and n is 1 when m is 1 and n is 0 when m is 2; and $R^3$ and $R^4$ each represents hydrogen or may—when m is 2—together represent a bond; and $R^5$ is —OH or $C_{1-6}$-alkoxy;

or a pharmaceutically acceptable salt thereof.

The compounds of formula I may exist as geometric and optical isomers and all isomers and mixtures thereof are included herein. Isomers may be separated by means of standard methods such as chromatographic techniques or fractional crystallization of suitable salts.

Preferably, the compounds of formula I exist as the individual geometric or optical isomers.

The compounds according to the invention may optionally exist as pharmaceutically acceptable acid addition salts or—when the carboxylic acid group is not esterified—as pharmaceutically acceptable metal salts or—optionally alkylated—ammonium salts.

Examples of such salts include inorganic and organic acid addition salts such as hydrochloride, hydrobromide, sulphate, phosphate, acetate, fumarate, maleate, citrate, lactate, tartrate, oxalate or similar pharmaceutically acceptable inorganic or organic acid addition salts, and include the pharmaceutically acceptable salts listed in Journal of Pharmaceutical Science, 66, 2 (1977) which are hereby incorporated by reference.

The term "$C_{1-6}$-alkyl" as used herein, alone or in combination, refers to a straight or branched, saturated hydrocarbon chain having 1 to 6 carbon atoms such as e.g. methyl, ethyl, n-propyl, isopropyl, n-butyl, sec-butyl, isobutyl, tert-butyl, n-pentyl, 2-methylbutyl, 3-methylbutyl, n-hexyl, 4-methylpentyl, neopentyl, n-hexyl, 1,2-dimethylpropyl, 2,2-dimethylpropyl and 1,2,2-trimethylpropyl.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "halogen" means fluorine, chlorine, bromine or iodine.

Illustrative examples of compounds encompassed by the present invention include:

(R)-1-(3-(6,11-Dioxo-6,11-dihydro-5H-dibenz[b,e] azepin-5-yl)-1-propyl)-3-piperidinecarboxylic acid;

(R)-1-(3-(6,11-Dihydro-5H-dibenz[b,e]azepin-5-yl)-1-propyl)-3-piperidinecarboxylic acid;

(R)-1-(3-(5,11-Dihydro-10H-dibenzo[b,e][1,4]diazepin-10-yl)-1-propyl)-3-piperidinecarboxylic acid;

(R)-1-(3-(11H-Dibenzo[b,f][1,4]thiazepin-10-yl)-1-propyl)-3-piperidinecarboxylic acid;

(R)-1-(3-(11H-Dibenz[b,f][1,4]oxazepin-10-yl)-1-propyl)-3-piperidinecarboxylic acid;

(R)-1-(3-(11H-Dibenz[b,f][1,4]oxathiepin-11-yl)-1-propyl)-3-piperidinecarboxylic acid;

(R)-1-(3-(11H-Dibenzo[b,e][1,4]dithiepin-11-yl)-1-propyl)-3-piperidinecarboxylic acid;

(R)-1-(3-(11H-Dibenz[b,e][1,4]oxathiepin-10-yl)-1-propyl)-3-piperidinecarboxylic acid;

(R)-1-(3-(11,12-Dihydro-10H-dibenz[b,g][1,5]oxazocin-11-yl)-1-propyl)-3-piperidinecarboxylic acid;

(R)-1-(3-(11,12-Dihydro-10H-dibenzo[b,g][1,5]thiazocin-11-yl)-1-propyl)-3-piperidinecarboxylic acid;

1-(3-(11,12-Dihydro-6H-dibenz[b,f]azocin-5-yl)-1-propyl)-3-piperidinecarboxylic acid; 1-(3-(11,12-Dihydro-5H-dibenzo[a,e]cycloocten-5-ylidene)-1-propyl)-3-piperidinecarboxylic acid;

1-(3-(6-Oxo-11,12-dihydro-5H-dibenz[b,f]azocin-5-yl)-1-propyl)-3-piperidinecarboxylic acid;

1-(3-(7,12-Dihydro-6H-dibenzo[a,d]cycloocten-6-ylidene)-1-propyl)-3-piperidinecarboxylic acid;

1-(3-(5-Methyl-5,11-dihydro-dibenz[b,f]azepin-10-ylidene)-1-propyl)-3-piperidinecarboxylic acid;

1-(3-(6-Oxo-5,11-dihydro-5H-dibenz[b,e]azepin-5-yl)-1-propyl)-3-piperidinecarboxylic acid;

(R)-1-(3-(11-Oxo-10,11-dihydro-5H-dibenzo[b,e][1,4] diazepin-10-yl)-1-propyl)-3-piperidinecarboxylic acid;

(R)-1-(3-(6-Oxo-11,12-dihydro-5H-dibenz[b,f]azocin-5-yl)-1-propyl)-3-piperidinecarboxylic acid;

(R)-1-(3-(10,11-Dihydro-dibenz[b,f][1,4]oxazepin-10-yl)-1-propyl)-3-piperidinecarboxylic acid;

(R)-1-(3-(5,6,11,12-Tetrahydro-dibenz[b,f]azocin-5-yl)-1-propyl)-3-piperidinecarboxylic acid;

(R)-1-(3-(11-Oxo-6,11-dihydro-5H-dibenz[b,e]azepin-5-yl)-1-propyl)-3-piperidine-carboxylic acid;

(R)-1-(3-(5-Methyl-dibenz[b,f]azepin-10-yl)-1-propyl)-3-piperidinecarboxylic acid;

(R)-1-(3-(6,7-Dihydro-5H-dibenz[b,g][1,5]oxazocin-6-yl)-1-propyl)-3-piperidinecarboxylic acid;

(R)-1-(3-(11,12-Dihydro-dibenz[a,e]cycloocten-5-yl)-1-propyl)-3-piperidinecarboxylic acid;

or a pharmaceutically acceptable salt thereof.

As used herein, the term "patient" includes any mammal which could benefit from treatment of neurogenic pain or inflammation or insulin resistance in NIDDM. The term particularly refers to a human patient, but is not intended to be so limited.

It has been demonstrated that the novel compounds of formula I inhibit neurogenic inflammation which involves the release of neuropeptides from peripheral and central endings of sensory C-fibres. Experimentally this can be demonstrated in animal models of formalin induced pain or paw oedema (Wheeler and Cowan, Agents Actions 1991, 34, 264–269) in which the novel compounds of formula I exhibit a potent inhibitory effect. Compounds of formula I may be used to treat all painful, hyperalgesic and/or inflammatory conditions in which C-fibers play a pathophysiological role by eliciting neurogenic pain or inflammation, i.e.:

Acutely painful conditions exemplified by migraine, postoperative pain, burns, bruises, post-herpetic pain (Zoster) and pain as it is generally associated with acute inflammation; chronic, painful and/or inflammatory conditions exemplified by various types of neuropathy (diabetic, post-traumatic, toxic), neuralgia, rheumatoid arthritis, spondylitis, gout, inflammatory bowel disease, prostatitis, cancer pain, chronic headache, coughing, asthma, chronic pancreatitis, inflammatory skin disease including psoriasis and autoimmune dermatoses, osteoporotic pain.

Further, it has been demonstrated that the compounds of general formula I improves the glucose tolerance in diabetic ob/ob mice and that this may result from the reduced release of CGRP from peripheral nervous endings. Hence the compounds of general formula I may be used in the treatment of NIDDM as well as aging-associated obesity. Experimentally this has been demonstrated by the subcutaneous administration of glucose into ob/ob mice with or without previous oral treatment with a compound of general formula I.

The compounds of formula I may be prepared by the following method:

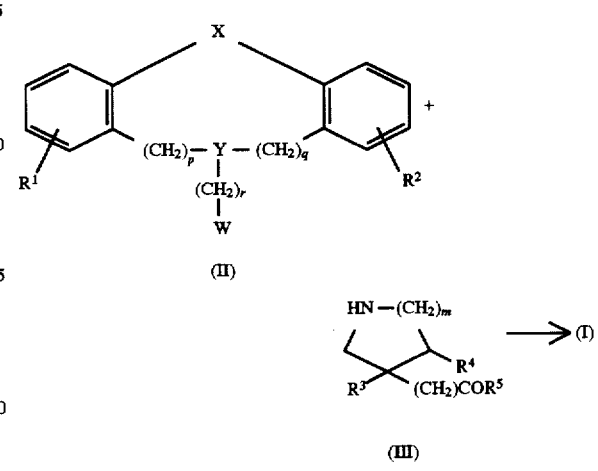

A compound of formula II wherein $R^1$, $R^2$, X, Y, p, q and r are as defined above and W is a suitable leaving group such as halogen, p-toluene sulphonate or mesylate may be reacted with an azaheterocyclic compound of formula III wherein $R^3$, $R^4$, $R^5$, m and n are as defined above. This alkylation reaction may be carried out in a solvent such as acetone, dibutylether, 2-butanone, methyl ethyl ketone, ethyl acetate, tetrahydrofuran (THF) or toluene in the presence of a base e.g. potassium carbonate and a catalyst, e.g. an alkali metal iodide at a temperature up to reflux temperature for the solvent used, for e.g. 1 to 120 h. If esters have been prepared in which $R^5$ is alkoxy, compounds of formula I wherein $R^5$ is OH may be prepared by hydrolysis of the ester group, preferably at room temperature in a mixture of an aqueous alkali metal hydroxide solution and an alcohol such as methanol or ethanol, for example, for about 0.5 to 6 h.

Compounds of formula II and III may readily be prepared by methods familiar to those skilled in the art.

Under certain circumstances it may be necessary to protect the intermediates used in the above methods e.g. a compound of formula III with suitable protecting groups. The carboxylic acid group can, for example, be esterified. Introduction and removal of such groups is described in "Protective Groups in Organic Chemistry" J. F. W. McOrnie ed. (New York, 1973).

Pharmacological Methods

Formalin induced pain or paw oedema

Values for in vivo inhibition of formalin induced pain or oedema for the compounds of the present invention were assessed in mice essentially by the method of Wheeler-Aceto and Cowan (Agents Action 1991, 34, 265–269).

About 20 g NMRI female mice were injected 20 ml 1% formalin into the left hind paw. The animals were then placed on a heated (31° C.) table, and the pain response was scored. After 1 h they were killed and bled. Left and right hind paws were removed and the weight difference between the paws was used as indication of the oedema response of the formalin injected paw.

Reduced release of CGRP ob/ob female mice, 16 weeks of age, where injected glucose (2 g/kg) subcutaneously. At times hereafter blood glucose was determined in tail venous blood by the glucose oxidase method. At the end of the study the animals were decapitated and trunck blood collected. Immunoreactive CGRP was determined in plasma by radio-immuno-assay. Two groups of animals were used. The one group was vehicle treated, whereas the other group received a compound of formula I via drinking water (100 mg/l) for five days before the test.

Values for inhibition of formalin induced pain response for some representative compounds are recorded in table 1.

TABLE 1

| Inhibition of formalin induced pain response at 0.1 mg/kg | |
| --- | --- |
| Example no. | % Pain inhibition |
| 1 | 13 |
| 2 | 34 |
| 3 | 36 |
| 4 | 28 |
| 6 | 22 |

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent.

The compounds of formula I may be administered in a pharmaceutically acceptable acid addition salt form or where possible as a metal or a lower alkylammonium salt. Such salt forms exhibit approximately the same order of activity as the free base forms.

This invention also relates to pharmaceutical compositions comprising a compound of formula I or a pharmaceutically acceptable salt thereof and, usually, such compositions also contain a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatine, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

Generally, the compounds of this invention are dispensed in unit dosage form comprising 50–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet which may be prepared by conventional tabletting techniques contains

| Core: | |
| --- | --- |
| Active compound (as free compound or salt thereof) | 100 mg |
| Colloidal silicon dioxide (Areosil ®) | 1.5 mg |
| Cellulose microcryst. (Avicel ®) | 70 mg |
| Modified cellulose gum (Ac-Di-Sol ®) | 7.5 mg |
| Magnesium stearate | |
| Coating: | |
| HPMC | approx. 9 mg |
| *Mywacett ® 9–40 T | approx. 0.9 mg |

*Acylated monoglyceride used as plasticizer for film coating.

The route of administration may be any route which effectively transports the active compound to the appropriate or desired site of action, such as oral or parenteral e.g. rectal, transdermal, subcutaneous, intranasal, intramuscular, topical, intravenous, intraurethral, ophthalmic solution or an ointment, the oral route being preferred.

EXAMPLES

The process for preparing compounds of formula I and preparations containing them is further illustrated in the following examples, which, however, are not to be construed as limiting.

Hereinafter, TLC is thin layer chromatography, CDCl₃ is deuterio chloroform and DMSO-d₆ is hexadeuterio dimethylsulfoxide. The structures of the compounds are confirmed by either elemental analysis or NMR, where peaks assigned to characteristic protons in the title compounds are presented where appropriate. $^1$H NMR shifts ($\delta_H$) are given in parts per million (ppm). M.p. is melting point and is given in °C. and is not corrected. Column chromatography was carried out using the technique described by W. C. Still et al, J. Org. Chem. (1978), 43, 2923–2925 on Merck silica gel 60 (Art. 9385). Compounds used as starting materials are either known compounds or compounds which can readily be prepared by methods known per se.

Example 1

(R)-1-(3-(11-Oxo-10,11-dihydro-5H-dibenzo[b,e][1,4]diazepin-10-yl)-1-propyl)-3-piperidinecarboxylic acid hydrochloride

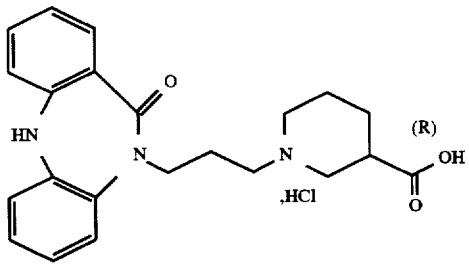

To a solution of 11-oxo-10,11-dihydro-5H-dibenzo[b,e][1,4]diazepine (12.1 g, 0.058 mol, prepared as described in *Synthesis*, 1985, 550) in dry N,N-dimethylformamide (150 ml) kept under an atmosphere of nitrogen, sodium hydride (2.8 g, 0.069 mol, 60% dispersion in oil) was added and the reaction mixture was stirred for 1 hour. 1-Bromo-3-chloropropane (10.9 g, 0.069 mol) was slowly added and the mixture was stirred overnight. The reaction mixture was quenched with water (200 ml) and extracted with diethyl ether (2×250 ml). The combined organic extracts were washed with water (3×300 ml), dried (MgSO₄) and the solvent was evaporated in vacuo. The solid was washed with heptane (100 ml), filtered off and dried, affording 11.1 g (67%) of 10-(3-chloropropyl)-5,10-dihydro-dibenzo[b,e][1,4]diazepin-11-one.

M.p. 127°–131° C.

$^1$H NMR (200 MHz, CDCl₃) $\delta_H$ 2.15 (m, 2H), 3.61 (t, 2H), 4.25 (t, 2H), 5.50 (bs, 1H, NH), 6.81 (d, 1 H), 6.91–7.13 (m, 4H), 7.20–7.26 (m, 2H), 7.82 (dd, 1H).

A mixture of the above chloride (4.0 g, 0.014 mol), (R)-3-piperidinecarboxylic acid ethyl ester tartrate (8.6 g, 0.028 mol), potassium carbonate (11.7 g, 0.084 mol), potassium iodide (4.6 g, 0.028 mol) and methyl ethyl ketone (100 ml) was heated at reflux temperature for 18 hours under an atmosphere of nitrogen. The cooled reaction mixture was quenched with water (100 ml) and extracted with diethyl ether (100 ml). The organic extract was washed with water (2×80 ml), saturated ammonium chloride (80 ml), dried (MgSO₄), filtered and the solvent was evaporated in vacuo. The crude product (7 g) was purified by column chromatography on silica gel (600 ml) using ethyl acetate as eluent. This afforded 3.1 g (55%) of (R)-1-(3-(11-oxo-10,11-dihydro-5H-dibenzo[b,e]-[1,4]diazepin-10-yl)-1-propyl)-3-piperidinecarboxylic acid ethyl ester as an oil.

TLC: $R_f$=0.24 (SiO₂: ethyl acetate).

$^1$H NMR (200 MHz, CDCl₃) $\delta_H$ 1.24 (t, 3H), 1.40 (m, 2H), 1.61 (m, 2H), 1.85 (m, 4H), 2.17 (d, 1H), 2.39 (m, 4H), 2.62 (bd, 1H), 2.82 (bd, 1H), 4.10 (q, 2H), 5.59 (bs, 1H, NH), 6.81 (d, 1H), 6.91–7.10 (m, 4H), 7.19–7.30 (m, 2H), 7.81 (dd, 1H).

The above ethyl ester (2.9 g, 7 mmol) was dissolved in a mixture of ethanol (50 ml) and water (30 ml). Sodium hydroxide (0.34 g, 9 mmol) was added and the reaction mixture was stirred for 40 hours at room temperature. The solvent was evaporated in vacuo, and water (150 ml) was added. The aqueous mixture was washed with diethyl ether (2×100 ml), acidified with concentrated hydrochloric acid and washed with dichloromethane (3×100 ml). The aqueous phase was evaporated in vacuo. The residue was suspended in a mixture of 2-propanol (10 ml) and diethyl ether (50 ml) and stirred for 60 hours at room temperature. The precipitate was filtered off, washed with diethyl ether and dried in vacuo. Yield 1.57 g (53%) of the title compound as an amorphous powder.

HPLC retention time=5.65 min. (5 µm C18 4×250 mm column, eluting with a mixture of water and acetonitril (7:3) containing phosphoric acid and buffered to pH=3 with triethylamine over 20 minutes at 35° C.).

$^1$H NMR (400 MHz, DMSO-d₆) $\delta_H$ 1.27 (m, 1H), 1.50 (d, 1H), 1.59–1.78 (m, 5H), 1.91 (m, 1H), 2.22 (t, 2H), 2.57 (d, 1H), 2.85 (d, 1H), 3.38 (m, 1H), 4.00 (t, 2H), 6.94 (t, 1H), 7.10 (m, 3H), 7.20 (m, 1H), 7.32 (m, 2H), 7.59 (d, 1H), 8.02 (s, 1H, NH).

By a similar procedure as described in Example 1 the following compound has been prepared:

Example 2

(R)-1-(3-(6-Oxo-11,12-dihydro-5H-dibenz[b,f]azocin-5-yl)-1-propyl)-3-piperidinecarboxylic acid hydrochloride

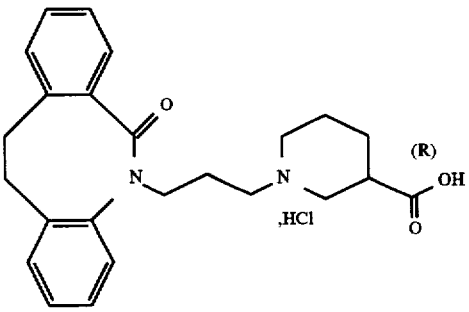

The title compound was prepared by a similar procedure as described in Example 1.

HPLC retention time=7.84 min (5 µm C18 4×250 mm column, eluting for 20 minutes at 30° C. with a mixture of water and acetonitril (7:3) containing phosphoric acid and buffered to pH=3 with triethylamine).

M.p. 223°–225° C.

MS(EI) 392.2 (M⁺–HCl, 10%)

Example 3

(R)-1-(3-(6,11-Dihydro-5H-dibenz[b,e]azepin-5-yl)-1-propyl)-3-piperidinecarboxylic acid hydrochloride

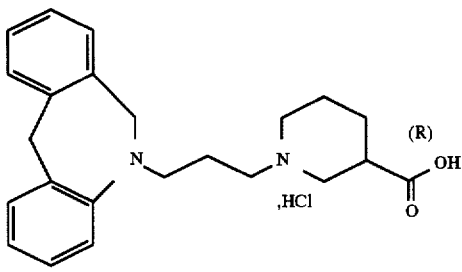

In a 100 ml round bottom flask equipped with magnetically stirring, thermometer, reflux condenser and addition funnel, 6,11-dihydro-5H-dibenz[b,e]azepine (1.0 g, 5.1 mmol, prepared in a similar way as described in Coll. Czech. Chem. Commun., 23, 1958, 1330) was dissolved in dry toluene (25 ml). 3-Chloropropionyl chloride (0.78 g, 6.1 mmol) was added slowly. When addition was complete, the reaction mixture was heated at 95° C. for 30 minutes and then allowed to cool to room temperature. With stirring, 0.2N sodium hydroxide (2.5 ml) was added. More toluene (50 ml) was added and the phases were separated. The organic phase was washed with 0.2N sodium hydroxide (10 ml) until pH>10, and then with water (3×10 ml) and brine (10 ml). After drying (MgSO$_4$), the solvent was evaporated in vacuo affording 3-chloro-1-(6,11-dihydro-5H-dibenz[b,e]azepin-5-yl)-1 -propanone as an oil which was obtained in quantitative yield and used for further reactions without purification.

A 1.0M tetrahydrofuran solution of lithium aluminum hydride (9.8 ml) was introduced under a nitrogen atmosphere to a dry 100 ml three-necked roundbottom flask using a syringe. Concentrated sulphuric acid (0.264 ml) was cautiously added under cooling on an ice bath, and the resulting solution was stirred at room temperature for 1.5 hour. The above amide was dissolved in dry tetrahydrofuran (9.8 ml) and slowly added. The reaction mixture was stirred overnight. The reaction was quenched by addition of water (0.4 ml), 4N sodium hydroxide (0.4 ml) and water (1.2 ml), successively. The resulting mixture was filtered (hyflo) and the filtercake was washed with diethyl ether and ethyl acetate. The solvent was evaporated affording 5-(3-chloropropyl)-6,11-dihydro-5H-dibenzo[b,e]azepine, which was used for further reaction without purification.

A solution of potassium iodide (4.5 g, 0.027 mol) in methyl ethyl ketone (75 ml) was heated at reflux temperature for 1 hour. A solution of the above chloride (1.2 g, 4.2 mmol) in methyl ethyl ketone (25 ml) was added and the reaction mixture was heated at reflux temperature for 2.75 hours. (R)-3-Piperidinecarboxylic acid ethyl ester tartrate (1.87 g, 6.2 mmol) and potassium carbonate (1.44 g, 0.01 mol) were added and the mixture was heated at reflux temperature for 24 hours, and left stirring at room temperature for 48 hours. After filtration on filter aid (celite), the solvent was removed by evaporation. The residue was purified by column chromatography on silica gel (125 g) using a mixture of heptane and ethyl acetate (1:1) as eluent. This afforded 0.7 g (42%) of (R)-1-(3-(6,11-dihydro-5H-dibenz[b,e]azepin-5-yl)-1-propyl)-3-piperidinecarboxylic acid ethyl ester as an oil.

TLC: R$_f$=0.19 (SiO$_2$: heptane/ethyl acetate=1:1).

The above ester (0.66 g, 1.7 mmol) was dissolved in ethanol (10 ml) and a solution of sodium hydroxide (0.25 g) in water (2 ml) was added. The mixture was stirred at room temperature for 2 hours and concentrated hydrochloric acid (0.8 ml) was added. Dichloromethane (100 ml) was added, followed by water (50 ml) and the phases were separated. The organic phase was dried (MgSO$_4$) and the solvent evaporated in vacuo. The residue was stripped with acetone, suspended in isopropyl acetate and filtered off. This afforded after drying, 0.5 g (74%) of the title compound as an amorphous solid.

HPLC retention time=20.41 minutes (5 µm C18 4×250 mm column, eluting with a 20–80% gradient of 0.1% trifluoroacetic acid/acetonitrile and 0.1% trifluoroacetic acid/water over 30 minutes at 35° C.).

Calculated for C$_{23}$H$_{28}$N$_2$O$_2$, HCl, 0.25 H$_2$O:

C, 68.14%; H, 7.28%; N, 6.91%; Found:

C, 68.08%; H, 7.44%; N, 6.61%.

Example 4

(R)-1-(3-(6,11-Dioxo-6,11-dihydro-5H-dibenz[b,e] azepin-5-yl)-1-propyl)-3-piperidine-carboxylic acid hydrochloride

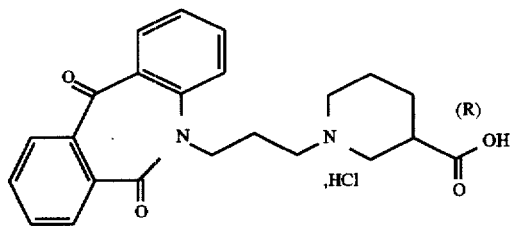

To a solution of 5H-dibenz[b,e]azepine-6,11-dione (3.0 g, 0.013 mol) in dry N,N-dimethylformamide (25 ml) kept under an atmosphere of nitrogen, sodium hydride (0.7 g, 0.027 mol, 60% dispersion in mineral oil) was added in portions and the reaction mixture was stirred for 1.5 hour. 1-Bromo-3-chloropropane (5.0 g, 0.031 mol) dissolved in N,N-dimethylformamide was slowly added and the mixture was stirred overnight. Ammonium chloride (2.0 g, 0.04 mol) was added and stirring was continued for 30 minutes. The solution was poured onto water (300 ml) and the mixture was extracted with dichloromethane (2×200 ml). The combined organic extracts were dried (MgSO$_4$), filtered and the solvent was evaporated in vacuo. The residue was purified by column chromatography on silica gel (150 g) using a mixture of heptane and ethyl acetate (4:1) as eluent to give 3.1 g (79%) of 5-(3-chloropropyl)-5H-dibenz[b,e]azepine-6,11-dione as an oil.

TLC: R$_f$=0.48 (SiO$_2$: heptane/ethyl acetate=1:1).

A solution of potassium iodide (10.0 g, 0.06 mol) in methyl ethyl ketone (180 ml) was heated at reflux temperature for 1 hour. A solution of the above chloride (3.09 g, 0.01 mol) in methyl ethyl ketone (20 ml) was added and the reaction mixture was heated at reflux temperature for 2 hours. After cooling to about 60° C., (R)-3-piperidinecarboxylic acid ethyl ester tartrate (4.50 g, 0.015 mol) and potassium carbonate (3.46 g, 0.025 mol) were added and the mixture was heated at reflux temperature for 48 hours. After cooling and filtration on filter aid (hyflo) the solvent was removed by evaporation. The residue was purified by column chromatography on silica gel (125 g) using first a mixture of heptane and ethyl acetate (1:1) to eluate the front running fractions and then with a mixture of heptane and ethyl acetate (2:3) as eluent. This afforded 1.21 g (29%) of (R)-1-(3-(6,11-dioxo-6,11-dihydro-5H-dibenz[b, e]azepin-5-yl)-1-propyl)-3-piperidinecarboxylic acid ethyl ester as an oil.

TLC: R$_f$=0.05 (SiO$_2$: heptane/ethyl acetate=2:3).

To the above ester (0.60 g, 1.4 mmol) in ethanol (10 ml), a solution of sodium hydroxide (0.35 g) in water (2 ml) was added. The mixture was stirred at room temperature for 2 hours and then concentrated hydrochloric acid (1 ml) was added. Dichloromethane (100 ml) was added, followed by water (50 ml) and the phases were separated. The organic phase was dried (MgSO$_4$) and the solvent was evaporated in vacuo. Subsequent re-evaporation with acetone and addition of isopropyl acetate afforded, after filtration and drying 0.2 g (23%) of the title compound as a solid.

HPLC retention time=16.76 minutes (5 µm C18 4×250 mm column, eluting with a 20–80% gradient of 0.1% trifluoroacetic acid/acetonitrile and 0.1% trifluoroacetic acid/water over 30 minutes at 35° C.).

$^1$H NMR (400 MHz, DMSO-d$_6$) $\delta_H$ 1.35 (m, 1H), 1.50 (m, 1H), 1.61 (m, 1H), 1.80 (m, 3H), 2.19 (m, 1H), 2.33 (m, 1H), 2.54 (m, 3H), 2.78 (d, 1H), 2.93 (d, 1H), 3.39 (m, 2H), 4.50 (bs, 1H), 6.40 (t, 1H), 6.81 (d, 1H), 6.93 (d, 1H), 7.27–7.34 (m, 2H), 7.53 (t, 1 H), 7.60 (t, 1H), 7.94 (d, 1H), 8.70 (bs, 1H).

Example 5

(R)-1-(3-(10,11-Dihydro-dibenz[b,f][1,4]oxazepin-10-yl)-1-propyl)-3-piperidinecarboxylic acid hydrochloride

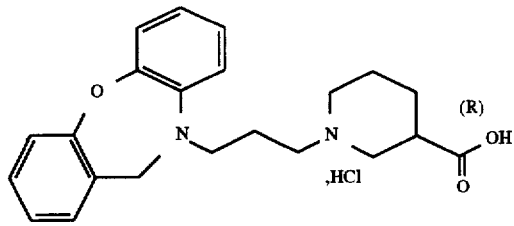

In a dry 250 ml three-necked flask equipped with reflux condenser and thermometer, lithium aluminum hydride (1.8 g, 0.047 mol) was suspended in dry diethyl ether (75 ml) under a nitrogen atmosphere. Cautiously, 10,11-dihydrodibenz[b,f][1,4]oxazepin-11-one (5.0 g, 0.024 mol) was added in portions. The mixture was heated at reflux temperature for 5 hours, cooled to room temperature and left stirring overnight. The reaction mixture was quenched by cautious addition of water (1.8 ml), 4N sodium hydroxide (1.8 ml) and finally water (5.4 ml). Diethyl ether and toluene were added and the mixture was filtered. The filtercake was washed with diethyl ether, toluene and ethyl acetate, successively. The filtrate was evaporated until dryness, affording 4.55 g (96%) of 10,11-dihydrodibenz[b,f][1,4]oxazepine.

The above tricycle (4.0 g, 0.02 mol) was dissolved in toluene (100 ml) and 3-chloropropionyl chloride (3.12 g, 0.025 mol) was added. The reaction mixture was heated at 95° C. for 30 minutes and left stirring for 1 hour. 0.2N Sodium hydroxide (10 ml) was added and the phases were separated. Toluene (200 ml) was added and the organic phase was washed with 0.2N sodium hydroxide (50 ml), water (3×50 ml) and brine (50 ml). The organic phase was dried (MgSO$_4$), filtered and the solvent evaporated. This afforded 3-chloro-1-(10,11-dihydro-dibenz[b,f][1,4]oxazepin-10-yl)-1-propanone in quantitative yield.

A 1.0M tetrahydrofuran solution of lithium aluminium hydride (38.4 ml, 0.0384 mol) was introduced into a dry 500 ml three-necked flask. Cautiously, concentrated sulphuric acid (1.84 ml, 0.019 mol) was added dropwise upon cooling on an icebath and then the mixture was stirred for 1.5 hour at room temperature. A solution of the above chloride in dry tetrahydrofuran (38.4 ml) was added dropwise and the reaction mixture was stirred for 1.5 hour. The reaction mixture was subsequently quenched by cautious addition of water (1.5 ml), 4N sodium hydroxide (1.5 ml) and finally water (4.5 ml), and the resulting suspension was left stirring overnight. The precipitated salt was filtered off and washed with diethyl ether, toluene and ethyl acetate. The filtrate was evaporated until dryness to give 4.8 g of crude 10-(3-chloropropyl)-10,11-dihydro-dibenz[b,f][1,4]oxazepine.

A solution of potassium iodide (16.0 g, 0.1 mol) in methyl ethyl ketone (180 ml) was heated at reflux temperature for 1 hour. A solution of the above chloride (3.14 g, 0.012 mol) in methyl ethyl ketone (20 ml) was added and the reaction mixture was heated at reflux temperature for 2.5 hours. (R)-3-Piperidinecarboxylic acid ethyl ester tartrate (7.2 g, 0.024 mol) and potassium carbonate (5.53 g, 0.04 mol) were added and the mixture was heated at reflux temperature for 72 hours. After cooling and filtration on filter aid (celite) the solvent was removed by evaporation. The residue was purified by column chromatography on silica gel (200 g) using a mixture of heptane and ethyl acetate (1:1) as eluent. This afforded 4.5 g (99%) of (R)-.1-(3-(10,11-dihydro-dibenz[b,f][1,4]oxazepin-10-yl)-1-propyl)-3-piperidinecarboxylic acid ethyl ester as an oil.

TLC: R$_f$=0.18 (SiO$_2$: heptane/ethyl acetate=1:1).

The above ester (1.0 g, 0.0025 mol) was dissolved in ethanol (15 ml) and a solution of sodium hydroxide (0.38 g) in water (3 ml) was added. The mixture was stirred at room temperature for 2 hours and concentrated hydrochloric acid (1.2 ml) was added. Dichloromethane (150 ml) was added, followed by water (50 ml) and the phases were separated. The organic phase was dried (MgSO$_4$) and the solvent evaporated in vacuo. Subsequent reevaporation with acetone and addition of a small amount of acetone followed by isopropyl acetate afforded, after filtration and drying 0.2 g (21%) of the title compound as a solid.

M.p. 185°–188° C.

Calculated for C$_{22}$H$_{26}$N$_2$O$_3$, HCl, 0.75 H$_2$O:

C, 63.46%; H, 6.85%; N, 6.73%; Found:

C, 63.06%; H, 6.74%; N, 6.47%.

Example 6

(R)-1-(3-(5,6,11,12-Tetrahydro-dibenz[b,f]azocin-5-yl)-1-propyl)-3-piperidinecarboxylic acid dihydrochloride

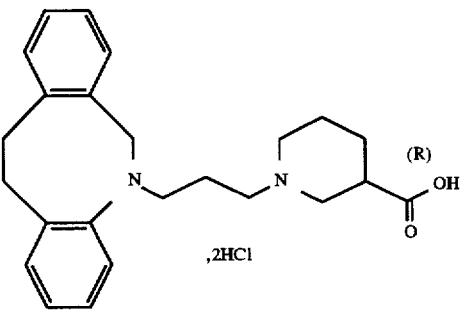

To a solution of 5,6,11,12-tetrahydro-dibenz[b,f]azocine hydrochloride (7.0 g, 0.029 mol) in dry tetrahydrofuran (100 ml) kept under an atmosphere of nitrogen, n-butyl lithium (22.2 ml, 0.06 mol, 2.7M in n-hexane) was added dropwise at 0° C. The reaction mixture was stirred at room temperature for 0.75 hour. A solution of 1-bromo-3-chloropropane (5.4 g, 0.034 mol) in dry tetrahydrofuran (100 ml) was added dropwise at 0° C. and the reaction mixture was stirred at room temperature for 4 hours. The reaction mixture was quenched with water (100 ml) and extracted with diethyl ether (100 ml). The organic extract was washed with brine (80 ml), dried (MgSO$_4$), filtered, and the solvent was evaporated in vacuo. Yield 7.7 g of crude 5-(3-chloropropyl)-5,6, 11,12-tetrahydro-dibenz[b,f]azocine.

A mixture of the above chloride (4.7 g, 0.027 mol), (R)-3-piperidinecarboxylic acid ethyl ester tartrate (16.6 g, 0.054 mol), dry potassium carbonate (22.3 g, 0.162 mol), potassium iodide (8.9 g, 0.054 mmol) and methyl ethyl ketone (250 ml) was heated at reflux temperature for 66 hours under an atmosphere of nitrogen. The cooled reaction mixture was quenched with water (250 ml) and extracted with diethyl ether (250 ml). The organic extract was washed with water (2×80 ml), brine (80 ml), dried (MgSO$_4$), filtered and the solvent was evaporated in vacuo. The crude product (12.4 g) was purified by column chromatography on silica gel (800 ml) using a mixture of ethyl acetate and heptane (1:2) as eluent. This afforded 3.3 g (30%) of (R)-1-(3-(5,6, 11,12-tetrahydro-dibenz[b,f]azocin-5-yl)-1-propyl)-3-piperidinecarboxylic acid ethyl ester as an oil.

TLC: R$_f$=0.35 (SiO$_2$: ethyl acetate/heptane=1:1).

The above ethyl ester (3.0 g, 7.38 mmol) was dissolved in a mixture of ethanol (30 ml) and water (30 ml). Sodium hydroxide (0.35 g, 8.85 mmol) was added and the reaction mixture was stirred for 18 hours at room temperature. The solvent was evaporated in vacuo and water (100 ml) was added. The aqueous mixture was washed with diethyl ether (2×100 ml) and acidified with concentrated hydrochloric acid. The aqueous phase was evaporated in vacuo and the residue was suspended in 2-propanol (25 ml) and filtered. The filtrate was evaporated in vacuo and the residue was dissolved in acetone (20 ml) and evaporated in vacuo. The residue was dissolved in dichloromethane (100 ml) and filtered. The filtrate was evaporated in vacuo and the residue was suspended in a mixture of acetone (10 ml) and diethyl ether (5 ml) and stirred for 18 hours at room temperature. The precipitate was filtered off, washed with diethyl ether and dried to afford 1.1 g (36%) of the title compound as a solid.

M.p. 200°–203° C.

Calculated for C$_{24}$H$_{30}$N$_2$O$_2$, 2HCl, H$_2$O:

C, 61.40%; H, 7.30%; N, 5.97%; Found:

C, 61.26%; H, 7.60%; N, 5.85%.

Example 7

(R)-1-(3-(11-Oxo-6,11-dihydro-5H-dibenz[b,e]azepin-5-yl)-1-propyl)-3-piperidine-carboxylic acid hydrochloride

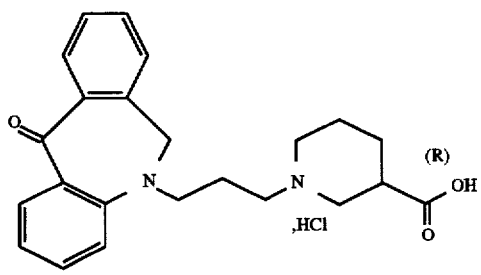

To a mixture of 5H-dibenz[b,e]azepine-6,11-dione (5.0 g, 22.4 mmol), ethylene glycol (12.5 ml, 0.224 mol) and nitromethane (60 ml) in dry toluene (100 ml) kept under an atmosphere of nitrogen, triflic acid (0.4 ml, 4.5 mmol) was added dropwise. The reaction mixture was heated at reflux temperature for 3 days with a water separator. The cooled reaction mixture was quenched with water (100 ml) and extracted with ethyl acetate (80 ml). The organic extract was washed with water (3×80 ml), dried (MgSO$_4$), filtered and the solvent was evaporated in vacuo. This afforded 5.16 g (86%) of 5H-dibenz[b,e]azepin- 6,11-dione 11-ethylene ketal as a solid.

TLC: R$_f$=0.32 (SiO$_2$: heptane/ethyl acetate=1:1).

$^1$H NMR (200 MHz, DMSO-d$_6$) δ$_H$ 3.75 (m, 2H), 4.17 (t, 2H), 7.06–7.80 (m, 8H), 10.58 (s, 1 H).

To a solution of the above ketal (4.5 g, 0.0168 mol) in dry N,N-dimethylformamide (75 ml) kept under an atmosphere of nitrogen, sodium hydride (0.8 g, 0.02 mol, 60% dispersion in mineral oil) was added in portions and the reaction mixture was stirred for 0.5 hour. A solution of 2-(3-bromo-1-propyloxy)tetrahydro-2H-pyran (4.5 g, 0.02 mol) in N,N-dimethylformamide was added slowly and the reaction mixture was stirred for 6 days. The reaction mixture was poured into water (100 ml) and the mixture was extracted with diethyl ether (2×100 ml). The combined organic extracts were washed with saturated ammonium chloride (3×100 ml), dried (MgSO$_4$), filtered and the solvent was evaporated in vacuo. This afforded a residue (6.7 g) which was purified by column chromatography on silica gel (800 ml) using a mixture of heptane and ethyl acetate (2:1) as eluent. This afforded 4.4 g (64%) of 5-(3-(tetrahydro-2H-pyran-2-yloxy)-1-propyl)-5H-dibenz[b,e]azepin-6,11-dione 11-ethylene ketal as an oil.

TLC: R$_f$=0.39 (SiO$_2$: heptane/ethyl acetate=1:1).

In a dry 100 ml three-necked flask equipped with reflux condenser and thermometer, lithium aluminum hydride (0.4 g; 10.5 mmol) was suspended in dry diethyl ether (50 ml) under a nitrogen atmosphere. Cautiously, a solution of 5-(3-tetrahydro-2H-pyran-2-yloxy)-1-propyl)-5H-dibenz[b,e]azepin-6,11-dione 11-ethylene ketal (3.9 g) in diethyl ether (30 ml) and tetrahydrofuran (20 ml) was added dropwise. The mixture was heated at reflux temperature for 3 hours, cooled to room temperature and quenched by cautious addition of water (0.5 ml) and 50% sodium hydroxide (0.5 ml), and filtered. The filtrate was evaporated until dryness affording 3.9 g of an oil which was purified by column chromatography on silica gel (600 ml) using a mixture of heptane and ethyl acetate (4:1) as eluent. This afforded 1.9 g (50%) of 5-(3-tetrahydro-2H-pyran-2-yloxy)-1-propyl)-5, 6-dihydro-dibenz[b,e]azepin-11-one ethylene ketal as an oil.

TLC: R$_f$=0.43 (SiO$_2$: heptane/ethyl acetate=2:1).

The above ketal (1.8 g, 4.55 mmol) was dissolved in 85% ethanol (20 ml) and concentrated hydrochloric acid (1 ml) was added. The reaction mixture was heated at reflux temperature for 3.5 hours. Water (100 ml) was added and the mixture was extracted with diethyl ether (2×100 ml). The combined organic extracts were washed with water (100 ml) and brine (100 ml), dried (MgSO$_4$) and filtered. The solvent was evaporated in vacuo to give 5-(3-hydroxy-1-propyl)-5, 6-dihydro-5H-dibenz[b,e]azepin-11-one in quantitative yield.

M.p. 113°–115° C.

To a mixture of the above alcohol (1.0 g, 3.7 mmol) and triethylamine (1 ml) in dichloromethane (30 ml), methanesulfonyl chloride (0.64 g, 5.61 mmol) dissolved in dichloromethane (10 ml) was added dropwise at 15° C. The reaction mixture was stirred at room temperature for 2 hours and quenched with water. The organic phase was separated, dried (MgSO$_4$), filtered and evaporated in vacuo. This afforded methanesulfonic acid 3-(11-oxo-5,6-dihydro-dibenz[b,e]azepin-5-yl)-1-propyl ester as an oil.

TLC: $R_f$=0.22 (SiO$_2$: heptane/ethyl acetate=1:1).

A mixture of the above methanesulfonate (1.3 g, 3.8 mmol), (R)-3-piperidinecarboxylic acid ethyl ester tartrate (2.3 g, 7.5 mmol), dry potassium carbonate (3.1 g, 23 mmol), and methyl ethyl ketone (50 ml) was heated at reflux temperature for 18 hours under an atmosphere of nitrogen. Potassium iodide (0.2 g, 1.2 mmol) was added and the mixture was heated at reflux temperature for 7 hours. After cooling, the reaction mixture was quenched with water (50 ml) and extracted with ethyl acetate (50 ml). The organic extract was washed with water (2×80 ml), brine (80 ml), dried (MgSO$_4$), filtered and the solvent was evaporated in vacuo. The crude product (1.4 g) was purified by column chromatography on silica gel (400 ml) using first a mixture of ethyl acetate and heptane (1:3) and then a mixture of ethyl acetate and triethylamine (96:4) as eluents. This afforded 0.9 g (59%) of (R)-1-(3-(11-oxo-5,6-dihydro-5H-dibenz[b,e]azepin-5-yl)-1-propyl)-3-piperidinecarboxylic acid ethyl ester as an oil.

TLC: $R_f$=0.12 (SiO$_2$: ethyl acetate/heptane=2:1).

To the above ester (0.8 g, 2.0 mmol) dissolved in ethanol (25 ml) a solution of sodium hydroxide (94 mg, 2.4 mmol) in water (15 ml) was added and the mixture was stirred at room temperature for 18 hours. The solvent was evaporated and water (75 ml) was added to the residue. The aqueous phase was washed with diethyl ether (2×75 ml), acidified to pH 1 with concentrated hydrochloric acid and washed with dichloromethane (3×100 ml). The aqueous phase was evaporated in vacuo and dichloromethane (400 ml) was added to the residue. The mixture was stirred for 18 hours, dried (MgSO$_4$), filtered and evaporated in vacuo. The residue was suspended in acetone (20 ml) and stirred for 18 hours. The solid was filtered off, washed with acetone and dried. This afforded 0.31 g (38%) of the title compound as a solid.

M.p. 221°–223° C.

Calculated for C$_{23}$H$_{26}$N$_2$O$_3$, HCl, 0.5H$_2$O:
C, 65.16%; H, 6.66%; N, 6.61%; Found:
C, 65.05%; H, 6.73%; N, 6.42%.

Example 8

(R)-1-(3-(5-Methyl-dibenz[b,f]azepin-10-yl)-1-propyl)-3-piperidinecarboxylic acid hydrochloride

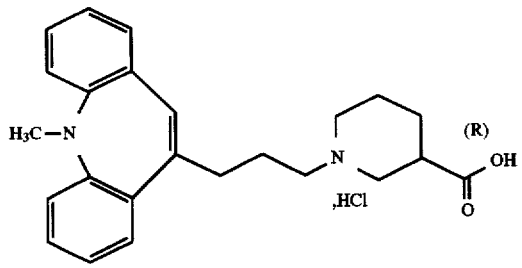

To a solution of 10-methoxy-5H-dibenz[b,f]azepine (40.7 g, 0.182 mol, prepared as described in Swiss pat. 389,619) in dry tetrahydrofuran (400 ml) kept under an atmosphere of nitrogen, n-butyl lithium (80 ml, 0.216 mol, 2.7M in n-hexane) was added dropwise at −30° C. The reaction mixture was stirred 0.5 hour. Iodomethane (13.3 ml, 0.214 mol) dissolved in dry tetrahydrofuran (50 ml) was added dropwise at −20° C. The reaction mixture was allowed to reach 0° C, quenched with water (300 ml) and extracted with diethyl ether (2×250 ml). The combined organic extracts were washed with water (500 ml), saturated brine (100 ml) and dried (MgSO$_4$), filtered and the solvent evaporated in vacuo. Yield 43.5 g (100%) of 5-methyl-10-methoxy-dibenz[b,f]azepine.

5-Methyl-10-methoxydibenz[b,f]azepine (43 g, 0.181 mol) was dissolved in 2N hydrochloric acid (800 ml) and heated at reflux temperature for 1.5 hour. The cooled reaction mixture was extracted with diethyl ether (2×400 ml). The combined organic extracts were washed with water (500 ml), saturated brine (100 ml) and dried (MgSO$_4$), filtered and the solvent was evaporated in vacuo. The crude product (39.5 g) was purified by column chromatography on silica gel (2×900 ml) using a mixture of ethyl acetate and heptane (10:1) as eluent. This afforded 21.5 g (53%) of 10,11-dihydro-5-methyl-dibenz[b,f]azepin-10-one.

M.p. 92°–93° C.

To an ethylmagnesium bromide solution (prepared from magnesium (2.3 g, 0.094 mol) and ethylbromide (8.1 ml, 0.103 mol) and dry tetrahydrofuran (50 ml)) cooled on an icebath, a solution of 3-chloro-1-propanol (7.9 ml, 0.094 mol) in dry tetrahydrofuran (50 ml) was added dropwise with stirring. After the addition was complete, the mixture was stirred for 0.5 hour. Magnesium (2.3 g, 0.094 mol) and an iodine crystal were added. Stirring was continued at reflux temperature for 1.5 hour. To this mixture a solution of 10,11-dihydro-5-methyl-dibenz[b,f]azepin-10-one (7.0 g, 0.031 mol) in dry tetrahydrofuran (75 ml) was added dropwise and the reaction mixture was stirred at reflux temperature for 2 hours. The cooled reaction mixture was quenched with saturated ammonium chloride (50 ml), water (50 ml) and extracted with ethyl acetate (2×100 ml). The combined organic extracts were washed with water (2×100 ml), saturated brine (100 ml) and dried (MgSO$_4$), filtered and the solvent was evaporated in vacuo. The crude product (7 g) was purified by column chromatography on silica gel (700 ml) using a mixture of ethyl acetate and heptane (1:2) as eluent. Yield 0.9 g (11%) of 3-(5-methyl-dibenz[b,f]azepin-10-yl)-1-propanol.

$^1$H NMR (200 MHz, CDCl$_3$) $\delta_H$ 1.90 (bs, 1H), 2.09 (dp, 2H), 3.32 (s, 3H), 3.88 (t, 2H), 4.16 (t, 2H), 6.04 (s, 1H), 6.91–7.34 (m, 7H), 7.45 (dd, 1H).

To a solution of 3-(5-methyl-dibenz[b,f]azepin-10-yl)-1-propanol (0.8 g, 3.01 mmol) and triethylamine (0.8 ml) in dichloromethane (25 ml), methanesulfonyl chloride (0.5 g, 4.52 mmol) dissolved in dichloromethane (5 ml) was added dropwise at 15° C. The reaction mixture was stirred at room temperature for 2 hours and quenched with water (25 ml). The organic phase was separated and dried (MgSO$_4$), filtered and evaporated in vacuo. This afforded 1.0 g (97%) of methanesulfonic acid 3-(5-methyl-dibenz[b,f]azepin-10-yl)-1-propyl ester as an oil.

TLC: $R_f$=0.49 (SiO$_2$: heptane/ethyl acetate=1:1).

A mixture of the above methanesulfonate (1.0 g, 2.91 mmol), (R)-3-piperidinecarboxylic acid ethyl ester tartrate (1.8 g, 5.82 mmol), dry potassium carbonate (2.4 g, 17.5 mmol), and methyl ethyl ketone (50 ml) was heated at reflux temperature for 18 hours under an atmosphere of nitrogen. Potassium iodide (0.2 g, 1.205 mmol) was added and the mixture was heated at reflux for an additional 18 hours. The cooled reaction mixture was quenched with water (50 ml) and extracted with ethyl acetate (50 ml). The organic phase was washed with water (2×80 ml), saturated brine (80 ml), dried (MgSO$_4$), filtered and the solvent evaporated in vacuo. The crude product (1.3 g) was purified by column chromatography on silica gel (500 ml) using a mixture of ethyl acetate and heptane (2:1) and later on a mixture of ethyl acetate and triethylamine (96:4) as eluents. This afforded 0.87 g (74%) of (R)-1-(3-(5-methyl-dibenz[b,f]azepin-10-yl)-1-propyl)-3-piperidine-carboxylic acid ethyl ester as an oil.

TLC: $R_f$=0.25 (SiO$_2$: ethyl acetate/heptane=2:1).

The above ester (0.7 g, 1.73 mmol) was dissolved in a mixture of ethanol (25 ml) and water (15 ml), sodium hydroxide (83 mg, 2.08 mmol) was added and the mixture was stirred at room temperature for 60 hours. The solvent was evaporated in vacuo and the residue dissolved in water (50 ml) and washed with diethyl ether (50 ml). The aqueous phase was acidified with concentrated hydrochloric acid until pH=1 and extracted with dichloromethane (3×100 ml). The combined dichloromethane phases were dried (MgSO$_4$) and the solvent evaporated in vacuo. The residue was suspended in a mixture of diethyl ether (10 ml) and acetone (10 ml) and stirred at room temperature for 18 hours. The solid was filtered off and washed with diethyl ether and dried. This afforded 0.15 g (20%) of the title compound as a solid.

M.p. 222°–224° C.

Calculated for $C_{24}H_{28}N_2O_2$, HCl, 1.25 H$_2$O:
C, 66.19%; H, 7.29%; N, 6.43%; Found:
C, 66.01%; H, 7.00%; N, 6.15%.

Example 9

(R)-1-(3-(6,7-Dihydro-5H-dibenz[b,g][1,5]oxazocin-6-yl)-1-propyl)-3-piperidine-carboxylic acid dihydrochloride

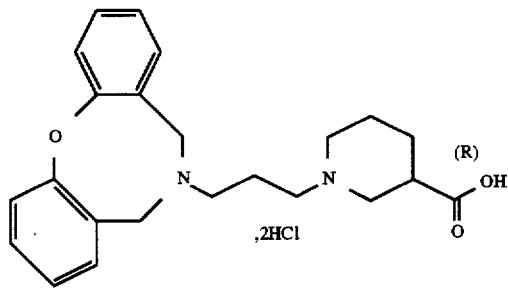

3-(6,7-Dihydro-5H-dibenz[b,g][1,5]oxazocin-6-yl)-1-propanol (0.60 g, 2.2 mmol, the compound is described in German Patent,, DE 2044508 710519 and prepared in a similar way as described in *J. Med. Chem.*, 11, 1968, 97 for an analogous azocine) was suspended in dry toluene (20 ml). On an ice bath and under a nitrogen atmosphere, triethylamine (0.9 ml) was added, followed by methansulfonyl chloride (0.3 ml) which was added dropwise. The resulting mixture was stirred at room temperature for 2 hours. Water (25 ml) was added followed by toluene (50 ml) and dichloromethane (50 ml). The phases were separated. The aqueous phase was extracted with ethyl acetate (50 ml). The combined organic phases were evaporated in vacuo. Methyl ethyl ketone (75 ml) was added to the residue, followed by (R)-3-piperidinecarboxylic acid ethyl ester tartrate (1.00 g, 3.3 mmol), potassium iodide (0.36 g, 2.2 mmol), and potassium carbonate (0.76 g, 5.5 mmol). The mixture was heated at reflux temperature for 216 hours. After filtration on filter aid (hyflo), the solvent was removed by evaporation in vacuo. The residue was purified by column chromatography on silica gel (150 ml) using ethyl acetate as eluent. This afforded 0.33 g (37%) of (R)-1-(3-(6,7-dihydro-5H-dibenz[b,g][1,5]oxazocin-6-yl)-1-propyl)-3-piperidinecarboxylic acid ethyl ester as an oil.

TLC: $R_f$=0.10 (SiO$_2$:ethyl acetate).

The above ester (0.19 g, 0.46 mmol) was dissolved in 96% ethanol (20 ml) and a solution of sodium hydroxide (0.57 g) in water (3 ml) was added. The mixture was stirred at room temperature for 2 hours and concentrated hydrochloric acid (0.4 ml) was added. Dichloromethane (100 ml) was added, followed by water (50 ml) and the phases were separated. The aqueous phase was washed with dichloromethane (2×75 ml) and evaporated in vacuo. Isopropanol was added to the residue and the mixture was filtered. The filtrate was evaporated in vacuo. The resulting solid was redissolved in isopropanol and isopropyl acetate was added. The precipitate was filtered off. This afforded after drying, 0.16 g (78%) of the title compound as an amorphous solid. The product was further purified for analysis by washing with first dichloromethane and then acetone.

M.p. amorph

Calculated for $C_{23}H_{28}N_2O_3$, 2 HCl, 1.1 H$_2$O:
C, 58.31%; H, 6.80%; N, 5.91%; Found:
C, 58.78%; H, 7.26%; N, 5.53%.

Example 10

(R)-1-(3-(11,12-Dihydro-dibenz[a,e]cycloocten-5-yl)-1-propyl)-3-piperidinecarboxylic acid hydrochloride

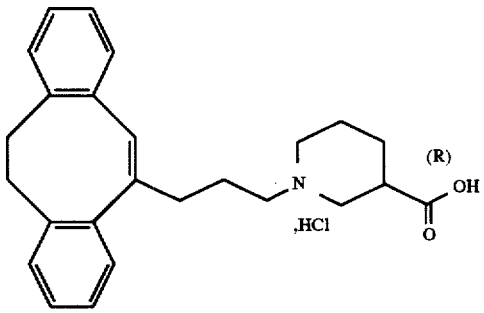

To a solution of sodium hydride (2.7 g, 0.066 mol, 60% dispersion in oil) in ethanol (200 ml) was added triethyl phosphonoacetate (14.9 g, 0.066 mol) and the reaction mixture was stirred at room temperature for 0.5 hour. To the reaction mixture was added 5,6,11,12-tetrahydro-dibenz[a,e]cycloocten-5-one (12.3 g, 0.055 mol, prepared as described in *J. Am. Chem. Soc.*, 77, 1955, 5078) and the reaction mixture was heated at reflux temperature for 18 hours. The solvent was evaporated in vacuo and the residue was suspended in water (200 ml) and extracted with diethyl ether (2×200 ml). The combined organic extracts were washed with water (2×80 ml), saturated ammonium chloride (80 ml), dried (MgSO$_4$), filtered and the solvent was evaporated in vacuo. The crude product (15.7 g) was purified by column chromatography on silica gel (800 ml) using a mixture of ethyl acetate and heptane (1:10) as eluent. This afforded 7.7 g (48%) of 11,12-dihydro-dibenz[a,e]cycloocten-5-acetic acid ethyl ester as an oil.

TLC: $R_f$=0.21 (SiO$_2$: ethyl acetate/heptane=1:10).

To a solution of lithiumaluminum hydride (1.9 g, 0.050 mol) in dry diethyl ether a solution of the above ester (7.3 g, 0.025 mol) in dry diethyl ether (50 ml) was added. The reaction mixture was stirred at reflux temperature for 1.5 hour. The reaction mixture was cooled on a ice bath and quenched by addition of water (2 ml), 20% sodium hydroxide (2 ml), and MgSO$_4$ successively. The resulting mixture was filtered and the filtercake was washed with diethyl ether (2×100 ml). The phases were separated and the organic phase was evaporated in vacuo affording 6.3 g (100%) of 2-(11,12-dihydro-dibenz[a,e]cycloocten-5-yl)-ethanol.

TLC: $R_f$=0.16 (SiO$_2$: ethyl acetate/heptane=1:4).

To a mixture of the above alcohol (6.0 g, 0.024 mol) and triethylamine (6 ml) in dichloromethane (100 ml), methanesulfonyl chloride (4.1 g, 0.036 mol) dissolved in dichloromethane (25 ml) was added dropwise at 15° C. The reaction mixture was stirred at room temperature for 2 hours and quenched with water (50 ml). The organic phase was separated, dried (MgSO$_4$) filtered and evaporated in vacuo. This afforded 7.7 g (98%) of methanesulfonic acid 2-(11, 12-dihydro-dibenz[a,e]cycloocten-5-yl)-1-ethyl ester as an oil.

A mixture of the above methanesulfonate (7.7 g), potassium cyanide (2.0 g, 0.031 mol), and dry dimethylsulfoxide (100 ml) was heated at 60° C. for 1.5 hour under an atmosphere of nitrogen. The cooled reaction mixture was quenched with water (100 ml) and extracted with diethyl ether (2×100 ml). The organic extract was washed with water (2×80 ml), brine (80 ml), dried (MgSO$_4$), filtered and the solvent was evaporated in vacuo affording 4.7 g (76%) of 3-(11,12-dihydro-dibenzo[a,e]cycloocten-5-yl)-propionitrile as an oil.

TLC: $R_f$=0.72 (SiO$_2$: ethyl acetate/heptane=1:2).

A mixture of the above propionitrile (3.6 g, 0.014 mol) and 50% potassium hydroxide was heated at reflux temperature for 42 hours. To the cooled reaction mixture water (300 ml) was added and the mixture was washed with diethyl ether (100 ml). The aqueous phase was acidified to pH=1 with concentrated hydrochloric acid and extracted with diethyl ether (2×200 ml). The combined organic extracts were washed with water (100 ml), brine (80 ml), dried (MgSO$_4$), filtered and the solvent was evaporated in vacuo affording 2.9 g (75%) of 3-(11,12-dihydro-dibenzo[a,e] cycloocten-5-yl)-1-propionic acid as an oil.

To a solution of lithiumaluminum hydride (0.7 g, 18 mmol) in dry tetrahydrofuran (30 ml) the above propionic acid (2.6 g, 9.3 mmol) in dry diethyl ether (30 ml) was added. The reaction mixture was stirred at reflux temperature for 1.5 hour. The reaction was cooled on a ice bath and quenched by addition of water (0.7 ml), and 20% sodium hydroxide (0.7 ml), successively. The resulting mixture was filtered and the filtercake was washed with diethyl ether (2×100 ml). The phases were separated and the organic phase was evaporated in vacuo affording 2.6 g (100%) of 3-(11,12-dihydro-dibenz[a,e]cycloocten-5-yl)-1-propanol as an oil.

TLC: $R_f$=0.34 (SiO$_2$: ethyl acetate/heptane=1:2).

To a mixture of the above alcohol (2.0 g, 7.56 mmol) and triethylamine (2 ml) in dichloromethane (50 ml), methanesulfonyl chloride (1.3 g, 11.4 mmol) dissolved in dichloromethane (10 ml) was added dropwise at 10° C. The reaction mixture was stirred at room temperature for 2 hours and quenched with water (50 ml). The organic phase was separated, dried (Na$_2$SO$_4$), filtered and evaporated in vacuo. This afforded 2.5 g of methanesulfonic acid 3-(11,12-dihydro-dibenz-[a,e]cycloocten-5-yl)-1-propyl ester as an oil.

A mixture of the above methanesulfonate (2.5 g), (R)-3-piperidinecarboxylic acid ethyl ester tartrate (4.6 g, 15.1 mmol), dry potassium carbonate (6.3 g, 45.4 mmol), and methyl ethyl ketone (100 ml) was heated at reflux temperature for 48 hours under an atmosphere of nitrogen. The cooled reaction mixture was quenched with water (100 ml) and extracted with diethyl ether (100 ml). The organic extract was washed with saturated brine (80 ml), dried (Na$_2$SO$_4$), filtered and the solvent evaporated in vacuo. The crude product (3.1 g) was purified by column chromatography on silica gel (600 ml) using a mixture of ethyl acetate/heptane (1:2) as eluent. This afforded 1.9 g of crude (R)-1-(3-(11,12-dihydro-dibenz[a,e]cycloocten-5-yl)-1-propyl)-3-piperidinecarboxylic acid ethyl ester. The ethyl ester was suspended in water (150 ml) and concentrated hydrochloric acid was added to pH=1. The aqueous phase was washed with diethyl ether (100 ml) basified to pH=8 with 20% sodium hydroxide and extracted with diethyl ether (2×100 ml). The combined organic extracts were washed with brine (80 ml), dried (MgSO$_4$), filtered and the solvent was evaporated in vacuo affording 1.1 g (36%) of (R)-1-(3-(11,12-dihydro-dibenz[a,e]cycloocten-5-yl)-1-propyl)-3-piperidinecarboxylic acid ethyl ester as an oil.

TLC: $R_f$=0.42 (SiO$_2$: ethyl acetate/heptane=1:1).

A solution of sodium hydroxide (120 mg, 3.0 mmol) in water (10 ml) was added to the above ester (1.0 g, 2.5 mmol) dissolved in ethanol (25 ml), and the mixture was stirred at room temperature for 60 hours. The solvent was evaporated in vacuo and to the residue water (100 ml) was added. The aqueous mixture was washed with diethyl ether (2×50 ml) acidified to pH=1 with concentrated hydrochloric acid and extracted with dichloromethane (3×75 ml). The combined organic extracts were dried (MgSO$_4$), filtered and evaporated in vacuo. This afforded 0.67 g (66%) of the title compound as a solid.

Calculated for C$_{25}$H$_{29}$NO$_2$, HCl, 0.25 H$_2$O:
C, 72.10%; H, 7.38%; N, 3.36%; Found:
C, 71.88%; H, 7.67%; N, 3.09%.

We claim:
1. A compound of formula I

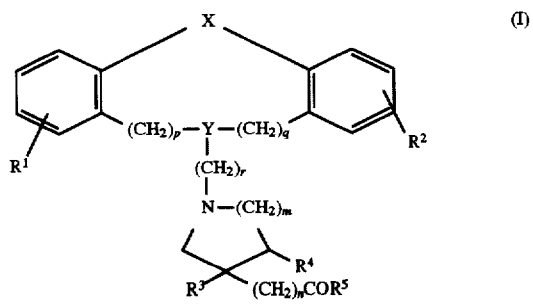

wherein
R$^1$ and R$^2$ independently are hydrogen, halogen, trifluoromethyl, hydroxy, C$_{1-6}$-alkyl or C$_{1-6}$-alkoxy;

Y is —CH$_2$—N—CH$_2$—, —CH$_2$—N—CH$_2$—, —(C=O)—N—CH$_2$—, or —CH$_2$—N—(C=O)—, wherein only the underscored atoms participate in the ring system;

X is —C(R$^6$R$^7$)—, —CH$_2$CH$_2$—, —CH=CH—CH$_2$—, —CH$_2$—CH=CH—, —CH$_2$—(C=O)—, —(C=O)—CH$_2$—, —CH$_2$CH$_2$CH$_2$—, —CH=CH—, —N(R$^8$)—(C=O)—, —(C=O)—N(R$^8$)—, —(C=O)—, or —N(R$^9$)— wherein R$^6$, R$^7$, R$^8$ and R$^9$ independently are hydrogen or C$_{1-6}$-alkyl, provided that the ring containing X and Y contains at least 8 members;

p is 0 or 1;
q is 0 or 1;
r is 1, 2 or 3;
m is 1 or 2;
n is 1 when m is 1 and n is 0 when m is 2;
R$^3$ and R$^4$ each represents hydrogen or may—when m is 2—together represent a bond;

and

R⁵ is —OH or $C_{1-6}$-alkoxy; or
a pharmaceutically acceptable salt thereof.

2. A compound according to claim 1 wherein R¹ and R² independently represent hydrogen, halogen or $C_{1-6}$-alkoxy.

3. A compound according to claim 2 wherein R¹ and R² are hydrogen.

4. A compound according to claim 1 wherein r is 2.

5. A compound according to claim 1 wherein m is 2.

6. A compound according to claim 1 wherein R⁵ is —OH.

7. A compound according to claim 1 which is:

1-(3-(11,12-Dihydro-6H-dibenz[b,f]azocin-5-yl)-1-propyl)-3-piperidinecarboxyliacid;

1-(3 -(6-Oxo-11,12-dihydro-5H-dibenz[b,f]azocin-5-yl)-1-propyl)-3-piperidinecarboxylic acid;

(R)-1-(3-(6-Oxo-11,12-dihydro-5H-dibenz[b,f]azocin-5-yl)-1-propyl)-3-piperidinecarboxylic acid;

(R)-1-(3-(5,6,11,12-Tetrahydro-dibenz[b,f]azocin-5-yl)-1-propyl)-3-piperidinecarboxylic acid; or
a pharmaceutically acceptable salt thereof.

8. A pharmaceutical composition comprising a compound according to claim 1 together with a pharmaceutically carrier or diluent.

9. The pharmaceutical composition according to claim 8 wherein the compound is present in an amount between 0.5 mg and 1000 mg per unit dose.

10. A method of treating diabetic neuropathy, migraine, neurogenic inflammation, or rheumatoid arthritis in a subject in need of such treatment comprising administering to the subject an effective amount of a compound according to claim 1.

11. A method of treating insulin resistance in a subject in need of such treatment comprising administering to the subject an effective amount of a compound according to claim 1.

12. A method of treating diabetic neuropathy, migraine, neurogenic inflammation, or rheumatoid arthritis in a subject in need of such treatment comprising administering to the subject a pharmaceutical composition according to claim 8.

13. A method of treating insulin resistance in a subject in need of such treatment comprising administering to the subject a pharmaceutical composition according to claim 8.

14. A compound of formula I

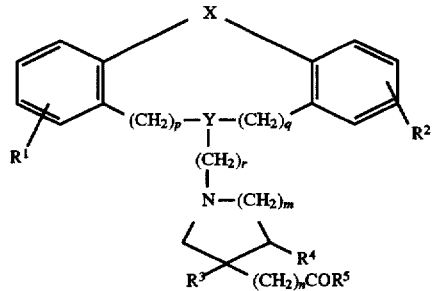

(I)

wherein

R¹ and R² independently are hydrogen, halogen, trifluoromethyl, hydroxy, $C_{1-6}$-alkyl or $C_{1-6}$-alkoxy;

Y is —CH=C—CH₂—, —CH₂—C=CH—, —CH₂—CH—CH₂—, —CH₂—CH—CH₂—, —CH₂—C=CH—, or —CH=C—CH₂—, wherein only the underscored atoms participate in the ring system;

X is —N(R⁸)—(C=O)—, —(C=O)—N(R⁸)—, or —N(R⁹)— wherein R⁸ and R⁹ independently are hydrogen or $C_{1-6}$-alkyl, provided that the ring containing X and Y contains at least 8 members;

p is 0 or 1;

q is 0 or 1;

r is 1, 2 or 3;

m is 1 or 2;

n is 1 when m is 1 and n is 0 when m is 2;

R³ and R⁴ each represents hydrogen or may—when m is 2—together represent a bond;

and

R⁵ is —OH or $C_{1-6}$-alkoxy; or
a pharmaceutically acceptable salt thereof.

15. A compound according to claim 14 wherein R¹ and R² independently represent hydrogen, halogen or $C_{1-6}$-alkoxy.

16. A compound according to claim 15 wherein R¹ and R² are hydrogen.

17. A compound according to claim 14 wherein r is 2.

18. A compound according to claim 14 wherein m is 2.

19. A compound according to claim 14 wherein R⁵ is —OH.

20. A pharmaceutical composition comprising a compound according to claim 14 together with a pharmaceutically carrier or diluent.

21. The pharmaceutical composition according to claim 20 wherein the compound is present in an amount between 0.5 mg and 1000 mg per unit dose.

22. A method of treating diabetic neuropathy, migraine, neurogenic inflammation, or rheumatoid arthritis in a subject in need of such treatment comprising administering to the subject an effective amount of a compound according to claim 14.

23. A method of treating insulin resistance in a subject in need of such treatment comprising administering to the subject an effective amount of a compound according to claim 14.

24. A method of treating diabetic neuropathy, migraine, neurogenic inflammation, or rheumatoid arthritis in a subject in need of such treatment comprising administering to the subject a pharmaceutical composition according to claim 20.

25. A method of treating insulin resistance in a subject in need of such treatment comprising administering to the subject a pharmaceutical composition according to claim 20.

* * * * *